(12) United States Patent
Remmerswaal et al.

(10) Patent No.: US 9,408,625 B2
(45) Date of Patent: Aug. 9, 2016

(54) SURGICAL CUTTING INSTRUMENT

(75) Inventors: Johannes Franciscus Marinus Remmerswaal, Delft (NL); Elinard Wilco Theuvenet, Delft (NL)

(73) Assignee: Ureca B.V., Rotterdam (NL)

( * ) Notice: Subject to any disclaimer, the term of this patent is extended or adjusted under 35 U.S.C. 154(b) by 679 days.

(21) Appl. No.: 13/380,146

(22) PCT Filed: Jun. 22, 2010

(86) PCT No.: PCT/NL2010/050382
§ 371 (c)(1),
(2), (4) Date: Jan. 24, 2012

(87) PCT Pub. No.: WO2010/151119
PCT Pub. Date: Dec. 29, 2010

(65) Prior Publication Data
US 2012/0130413 A1 May 24, 2012

(30) Foreign Application Priority Data

Jun. 22, 2009 (NL) .................................... 2003063

(51) Int. Cl.
*A61B 17/22* (2006.01)
*A61B 17/3207* (2006.01)
*A61B 17/3205* (2006.01)
(Continued)

(52) U.S. Cl.
CPC ....... *A61B 17/3207* (2013.01); *A61B 17/32056* (2013.01); *A61B 17/320725* (2013.01); *A61B 2017/003* (2013.01); *A61B 2017/00252* (2013.01); *A61B 2017/22038* (2013.01); *A61B 2017/22044* (2013.01); *A61B 2017/22094* (2013.01); *A61B 2017/22095* (2013.01); *A61B 2017/32006* (2013.01); *A61B 2017/320733* (2013.01)

(58) Field of Classification Search
CPC .................... A61B 17/3207; A61B 17/32056; A61B 17/320725; A61B 2017/22095; A61B 2017/320733; A61B 2017/22094; A61B 2017/32006; A61B 2017/003
USPC ........................ 600/37, 39; 606/159, 167–170
See application file for complete search history.

(56) References Cited

U.S. PATENT DOCUMENTS 3,910,279 A * 10/1975 Okada et al. ..................... 606/47
4,325,374 A * 4/1982 Komiya ......................... 606/47
5,312,341 A * 5/1994 Turi ......................... 604/103.05
(Continued)

FOREIGN PATENT DOCUMENTS

WO 2008/035330 A2 3/2008
WO 2009/082228 A1 7/2009

OTHER PUBLICATIONS

International Search Report, dated Jan. 18, 2011, from corresponding PCT application.

*Primary Examiner* — Ashley Fishback
(74) *Attorney, Agent, or Firm* — Foley & Lardner LLP; Sunit Talapatra

(57) ABSTRACT

Catheter assembly in which the catheter sleeve is provided with a flexible tip at its distal end for carrying out medical procedures. In order to be able to vary the position of the free end of the flexible tip, a control element is present consisting of an actuating wire. The actuating wire is attached to the free end of the flexible tip and extends externally with respect to the flexible tip, in the direction of the catheter, and then passes through an opening into the inside of the catheter to the proximal end thereof.

20 Claims, 6 Drawing Sheets

(51) Int. Cl.
*A61B 17/00* (2006.01)
*A61B 17/32* (2006.01)

(56) References Cited

U.S. PATENT DOCUMENTS

| | | | |
|---|---|---|---|
| 5,904,679 A * | 5/1999 | Clayman | 606/39 |
| 5,954,713 A | 9/1999 | Newman et al. | |
| 6,379,319 B1 * | 4/2002 | Garibotto et al. | 600/585 |
| 6,712,817 B1 * | 3/2004 | Goto et al. | 606/47 |
| 2002/0123698 A1 | 9/2002 | Garbotto et al. | |
| 2007/0083220 A1 | 4/2007 | Shamay | |
| 2007/0088369 A1 * | 4/2007 | Shaw | A61B 17/32056 606/113 |
| 2008/0091196 A1 | 4/2008 | Deal | |
| 2009/0093674 A1 * | 4/2009 | Adams | 600/104 |
| 2009/0093829 A1 | 4/2009 | Melsheimer et al. | |

* cited by examiner

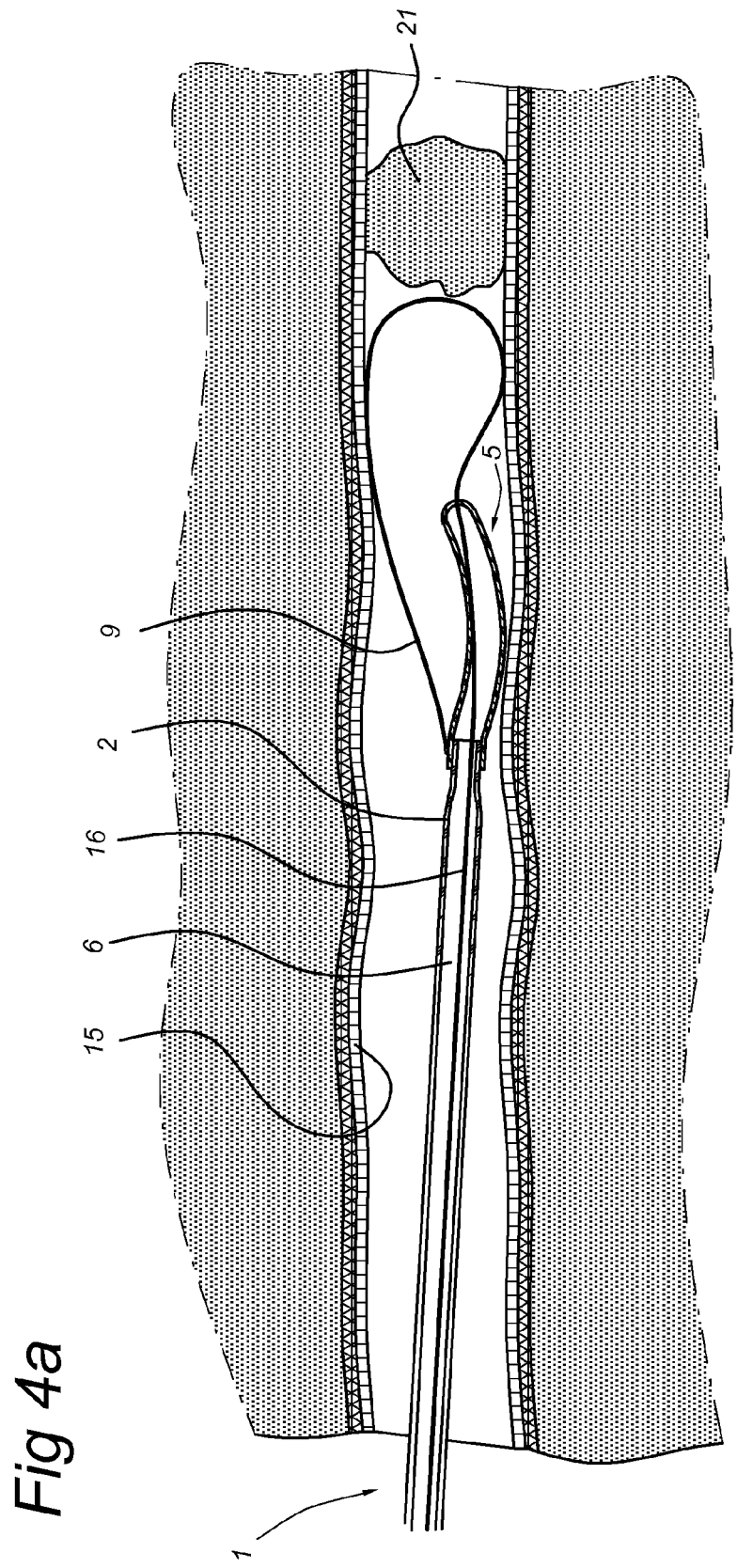

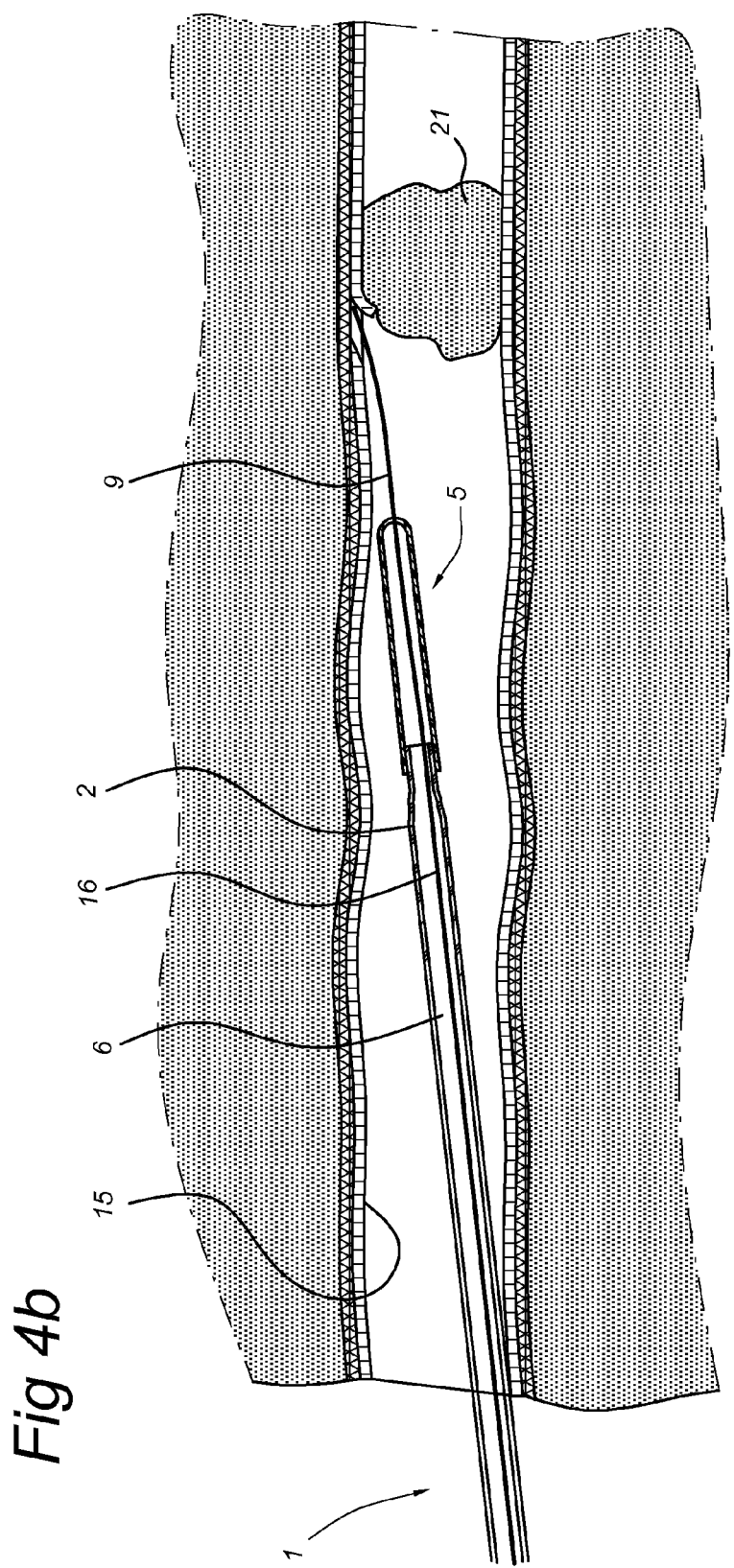

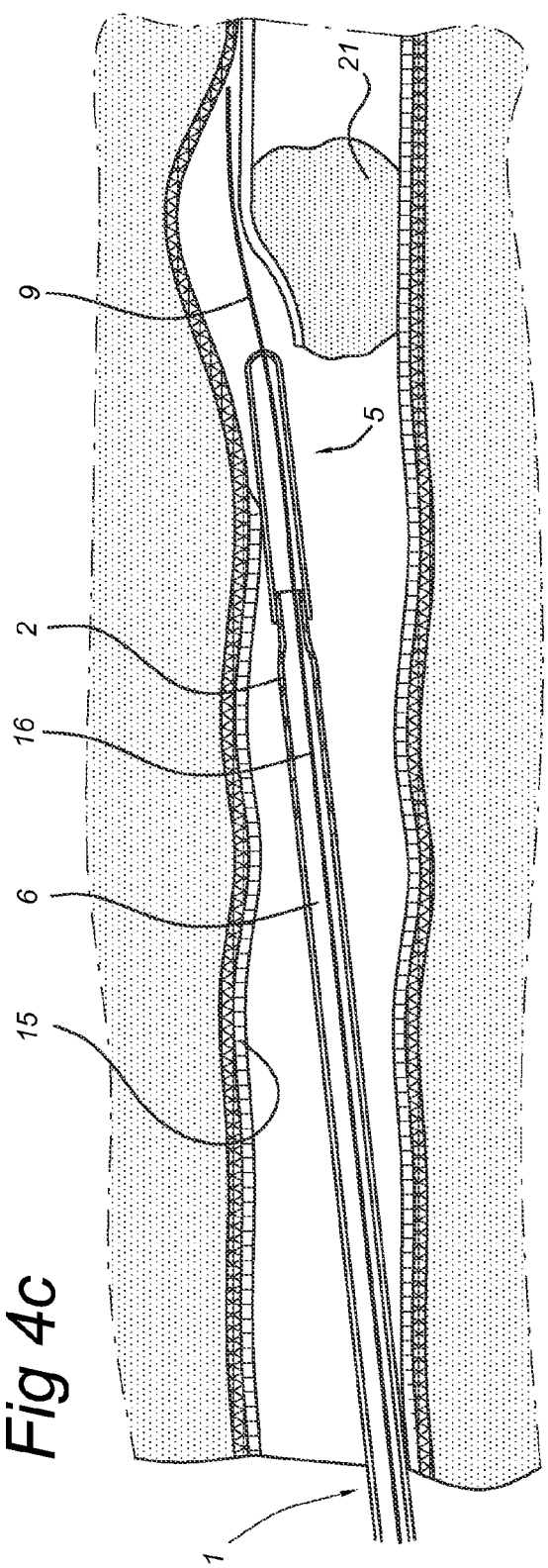
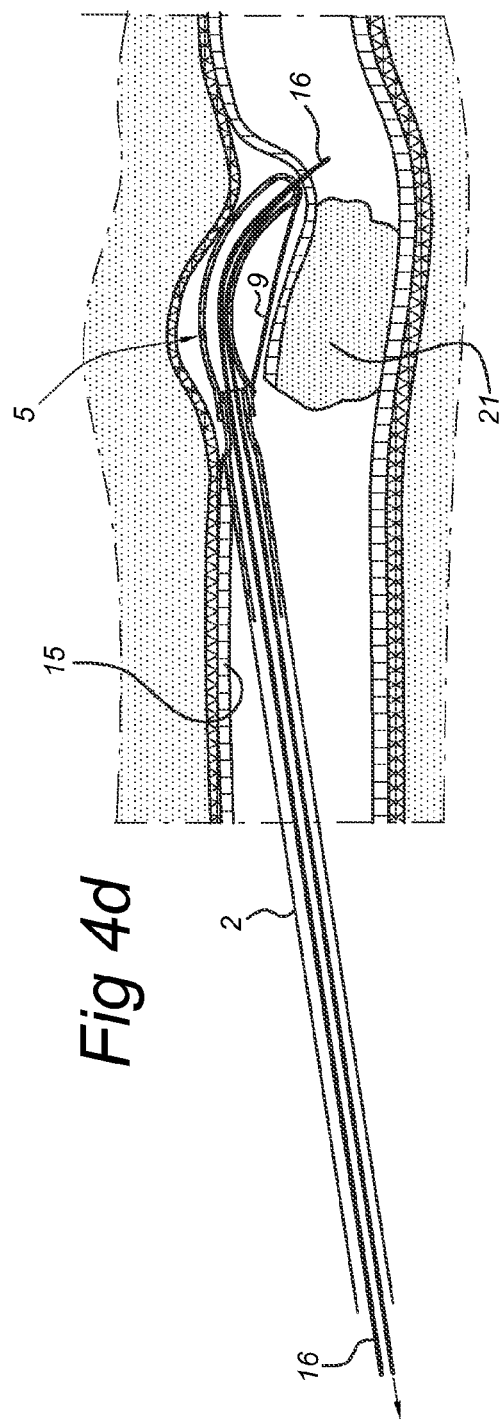

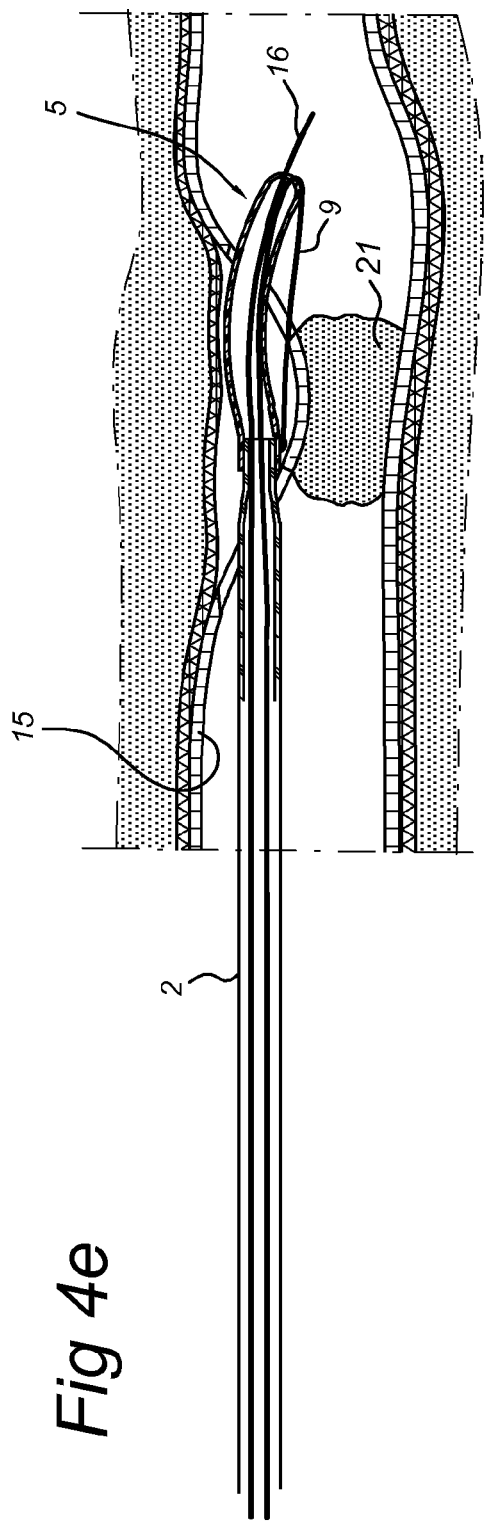
Fig 4e
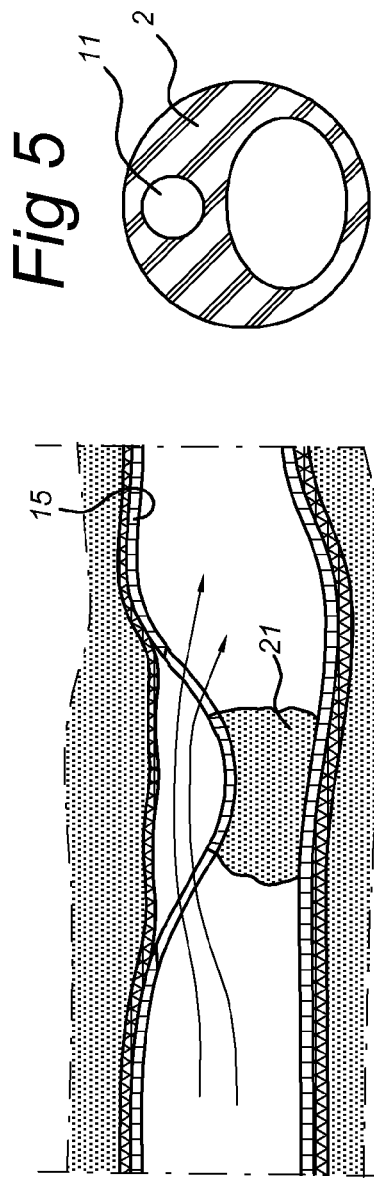
Fig 5
Fig 4f

SURGICAL CUTTING INSTRUMENT

The present invention relates to a surgical cutting instrument for passing occlusions, comprising a sleeve-shaped part having a proximal part and a distal part, and a cutting wire, wherein said sleeve-shaped part is provided with a lumen for guiding said cutting wire, which cutting wire extends in the form of a loop of adjustable size from the free end of said distal part of said sleeve, wherein the other end of said cutting wire extends outside said sleeve and is in contact with the distal part at a distance from the free end of the distal part of the sleeve.

Such a cutting instrument is known from the application PCT/NL 2008/050844 which is not a prior publication. The cutting instrument described in the latter is used in particular for passing occlusions in for example veins or arteries. To this end, the cutting instrument is introduced into the respective vessel and the occlusion is passed at the location of the occlusion with the cutting wire. The construction is embodied such that the cutting wire can be manipulated very well, both with regard to the position thereof and to the stiffness thereof.

This cutting instrument represents a significant improvement compared to the prior art. However, there are still situations where an occlusion can not be passed or can not be passed sufficiently quickly.

It is an object of the present invention to present an improved surgical cutting instrument by means of which the area of use for passing occlusions is further extended.

This object is achieved with the above-described surgical cutting instrument in that the distal part of the sleeve, from the free end thereof across a distance of at least 2 mm and at most 10 cm, is embodied to be substantially more flexible than the remaining part of the sleeve and said cutting wire is arranged such that when a force is exerted thereon, said cutting wire changes the curvature of said distal part.

Due to the presence of the distal end which is significantly more flexible than the other part of the sleeve, it is possible to adjust the curvature of this distal end and a surgical cutting instrument is obtained of which in particular the distal end can be bent into a certain position. As a result thereof, a passing movement of, for example, an occlusion can be supported. This applies more particularly to "returning" into the vein. After all, in certain circumstances, as is described in PCT/NL2008/050844, passing of an occlusion consists of the cutting instrument exiting the vein or artery by moving between tissue tubes of the veins past the occlusion. Subsequently, after the occlusion has been passed, the cutting instrument has to re-enter the vein or artery and it has been found that the flexibility of the distal part of the sleeve is very important therein.

In addition, it is possible, by moving the end of the distal end to and fro in a direction which is not the longitudinal direction of the cutting instrument, to remove material from, for example, an occlusion or to displace the latter by a kind of scraping movement and thus to create the optimum position for the free end of the distal part of the sleeve to return in the vessel by means of the puncture wire or by moving the sleeve longitudinally forward. In this position, the above-described cutting wire can become operational again in order to pass the occlusion. The cutting wire influences the curvature of the distal part. According to an advantageous embodiment of the invention, a part of the cutting wire is to this end provided so as to extend outside said distal part. More particularly, the cutting wire extends beyond the free end of the distal part as a loop, with part of the loop extending in the interior of the distal part via the free end of the distal part and the other end being situated outside thereof. The other end which is situated outside thereof can be attached to the free end of the distal part at a distance therefrom. However, it is also possible for an opening to be present at a distance from the free end of the distal part through which the cutting wire is passed inside. In a particular embodiment, it is also possible for the distal part of the sleeve to consist of a co-extrudate, the outside of which is softer than the inside.

Depending on the situation, it is possible for the cutting wire extending from the free end of the distal part in the distal part, to either extend through the sleeve towards the proximal part or to be attached at the distal part.

In any case, at least one end of the cutting wire has to be present at the proximal part in order to manipulate the cutting wire as such, that is to say to increase and reduce the size of the cutting loop which is produced by means thereof and to exert tension in order to bend the distal part.

Due to the fact that, according to a preferred embodiment of the invention, the cutting wire extends outside of the distal part, this embodiment allows for a highly accurate curvature of the distal part. As a result thereof, it is possible, for example by applying a simple tensile force to the cutting wire, to achieve an accurately determined displacement of the distal part. In addition, markings are preferably present so that the user has an indication at the proximal end in which direction the distal part bends.

According to a particular embodiment of the present invention, two cutting wires are present which, in top view and/or end-side view, are at an angle to one another. These can each effect the curvature of the distal end. Such a construction is advantageous because it can be used to limit the rotation of the sleeve. After all, as has been described above, when passing a certain kind of occlusion in veins and/or arteries, the cutting loop will function in a certain plane which is tangential to the circumferential surface of the vein. However, if the distal part has to be bent in order to enter the vein again, this curvature has to take place in a plane at right angles thereto, as a result of which it is necessary to move the cutting wire in the sleeve and rotate it through 90°, following which the distal end can be bent with the cutting wire in the direction in which the vein or artery is entered again. By placing two cutting wires at an angle to one another, one cutting wire can be used in order to force the passage between tissue layers which surround the vein or artery and the other wire can be used to displace the distal end in a direction, for example, at right angles thereto for re-entering the vein or artery.

Apart from the cutting wire or cutting wires described here, other wires may be present in the sleeve. These are preferably present in a separate lumen provided in the sleeve. An example thereof is a guide wire. Such a guide wire is used in order to for example guide the sleeve through a vein and consists of relatively easy bendable material. More particularly, it consists of a helically wound material. This makes it possible to move therethrough up to the occlusion without damaging the vein or artery. Another example of a wire which can be used in the sleeve adjacent to the cutting wire is a puncture wire. This has a relatively rigid end which can be used to carry out a piercing operation.

By means of such further wires, it is possible to cause or support the above-described difference in flexibility of the sleeve parts. Using a relatively stiff guide wire in combination with a relatively flexible sleeve will result in the combination being stiffer where the guide wire is present than where the guide wire is absent.

According to a particular embodiment of the present invention, the puncture wire and the guide wire are combined by providing a single wire, one end of which has the properties of a guide wire and the other end of which has the properties of a puncture wire. As a result thereof, the end which protrudes from the sleeve and serves as a guide wire can be removed therefrom after the distal end of the sleeve has reached the occlusion site and the wire can simply be turned around, in which case the puncture part protrudes from the distal end of the sleeve and can thus be used.

In addition to the indication for the direction of the curvature, it is possible to provide further indications on the proximal end which indicate the displacement of the cutting wire or cutting wires and the above-described guide wire/puncture wire with respect to the free end of the distal part as a result of which the operator knows precisely which movements are taking place. In addition, radiopaque material can be used, in particular for the distal part of the sleeve, so that the positioning of the distal part in the respective part of the body can be observed accurately during medical procedures.

The cutting wire or cutting wires can be fitted in the manner described in PCT/NL 2008/050844.

The present invention also relates to a method for passing an occlusion in a vein comprising introducing a surgical cutting instrument as described above into a vein, providing a passage through/past said occlusion by means of the cutting wire of the surgical cutting instrument and subsequently entering said vein, said entering the vein comprising curving of said distal part by operating said cutting wire.

According to a particular embodiment of the present method, it is possible to effect a kind of scraping movement using the free end of the distal part by successively bending the latter to a greater or lesser degree.

The invention will be explained below with reference to an exemplary embodiment illustrated in the drawing, in which:

FIGS. 4a-4f show diagrammatic views of the introduction of the surgical cutting instrument into a vessel and the passing of an occlusion;

FIG. 5 shows a cross section of the sleeve and

Figure 1:
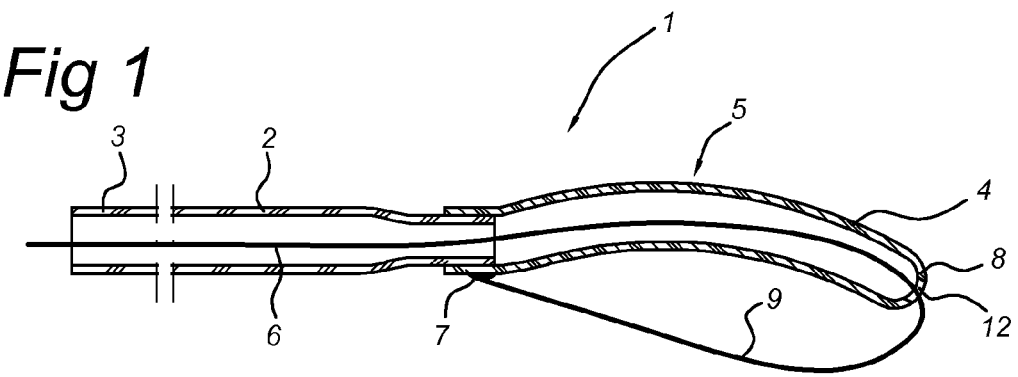
FIG. 1 shows a cross section of an embodiment of the surgical cutting instrument according to the invention.

In FIG. 1, a surgical cutting instrument according to a first embodiment of the invention is denoted overall by reference numeral 1. The cutting instrument inter alia consists of the sleeve 2 with a flexible tip 5 attached thereto. The tip has a limited length, typically (depending on the medical use) of between 2 mm and 10 cm, in particular 3-25 mm. The sleeve 2 consists of slightly stiffer material, which is nevertheless sufficiently flexible for the intended use. This means that if occlusions in veins have to be passed, the sleeve 2 is still sufficiently flexible to be passed through veins. The flexible tip 5 is significantly more flexible than the sleeve 2. The distal end of the flexible tip 5 is denoted by reference numeral 4, while the proximal end of the cutting instrument is denoted by reference numeral 3. Cutting wire 6 extends from the proximal end on the inside of the sleeve 2 through the outlet opening 12. Subsequently, the cutting wire 9 extends externally with respect to the flexible tip 5 which can be curved and is attached thereto near the end of the sleeve, for example at the position indicated in FIG. 1 by reference numeral 7. It will be understood that the attachment at 7 can also be more distal or more proximal. It is likewise possible for the cutting wire to exit through an opening at 7 and to be attached to the flexible tip 5 at 8. In any case, at least one end of the cutting wire extends up to the proximal actuating end.

In a specific embodiment, at least that part 9 of the cutting wire 6 which extends outside the catheter can be made from a relatively soft and slack material. FIG. 1 shows the non-tensioned state of the cutting wire 6. The flexible tip 5 can be embodied such that it is substantially slack and does not have a preferred position. In other embodiments, as is illustrated in FIG. 1, for example, the flexible tip is provided with a prefabricated curvature.

Near the proximal end 3 of the catheter assembly 2, indicating means (not shown) may be present which illustrate the mutual position of the cutting wire 6, more particularly of that part which protrudes from the catheter sleeve 2, and the sleeve. In addition, indicating means may be present at the proximal end which indicate in which direction the flexible tip is bent. This may, for example, be achieved by means of a longitudinal line which is provided on the sleeve 2 which indicates the location of the greatest or smallest curvature of the flexible tip (top or bottom side, as illustrated in FIG. 1).

Figure 2:
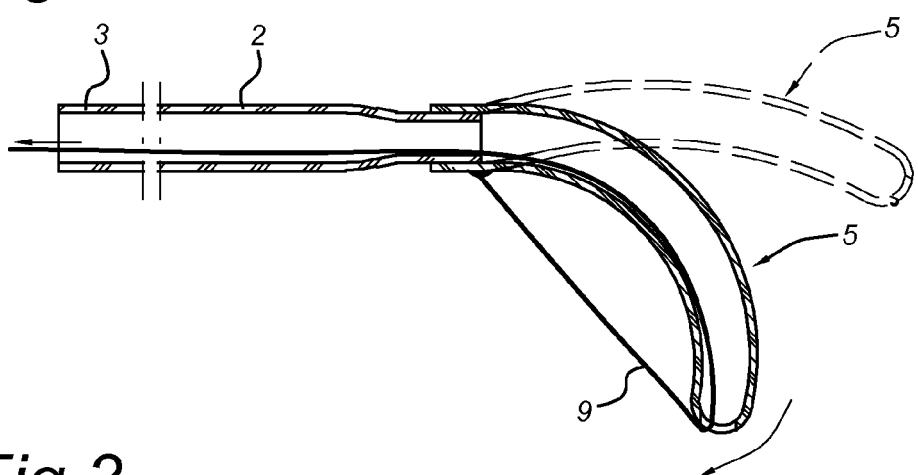
FIG. 2 shows a cross section of the surgical cutting instrument from FIG. 1 when the actuating wire is activated.

FIG. 2 shows the position in which a tensile force is exerted on the pulling or actuating wire 6 from the proximal end 3 of the cutting instrument 1. First, wire portion 9 is pulled straight and then exerts a tensile force on the distal end of the flexible tip 5, as a result of which the latter experiences a larger curvature, as is illustrated in FIG. 2.

Figure 3:
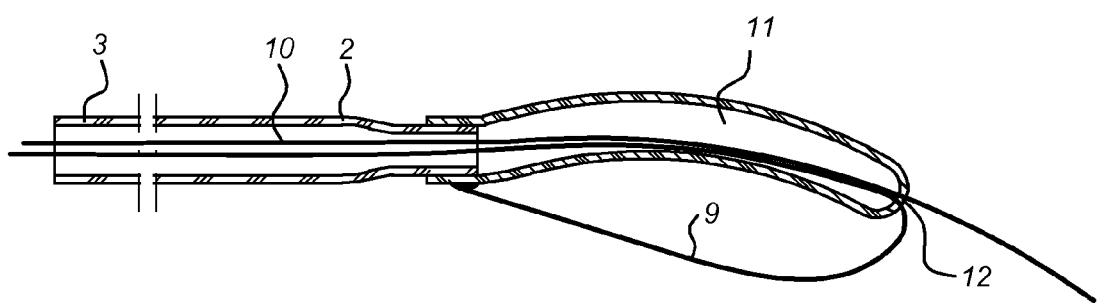
FIG. 3 shows a cross section of the surgical cutting instrument from the previous figures designed as a catheter with a further wire.

FIG. 3 shows a catheter assembly which is composed of the sleeve, as described with reference to FIGS. 1 and 2. The flexible tip 5 is provided with a further duct 11 with an outlet opening 12 through which a wire 10 can extend. It should be understood that the outlet opening 12 which, in the present case is depicted on the head end face of the distal end of the flexible tip, can also be located in another position, for example somewhere along the longitudinal extension of the flexible tip. In addition, such an outlet opening can extend at an angle to the longitudinal axis of duct 11 in order to preorient a wire which is to be moved therethrough.

Such a wire 10 may be a guide wire or a puncture wire. The embodiment of the wire depends on the intended use.

It is possible to use a single wire, one end of which acts as a puncture wire and the other end of which serves as a guide wire.

FIGS. 4a-4f illustrate how a guide wire 16 is first introduced into a vein or artery 15, followed by the cutting instrument 1 according to the present invention. The destination site of the distal part is indicated diagrammatically by reference numeral 21 in the figures. At the destination site, there is an occlusion which has to be passed by the cutting instrument. According to the present invention, the cutting instrument, when it is being introduced into the vein or artery, already comprises the cutting wire 6 by means of which the curvature of the tip 5 can be changed in the above-described manner.

FIGS. 4b and c show that a relatively stiff end of the cutting wire 6 can be used to penetrate the vein wall 15. In this case, FIGS. 4b and 4c are rotated through 90° with respect to FIG. 4a, that is to say the cutting loop 9 is situated in a plane at right angles to the drawing. FIG. 4c shows that when the sleeve is pushed further between the tissue layers of the vessel beyond the occlusion, it is difficult to penetrate the vessel wall on the other side of the occlusions and to re-enter the vessel. By now rotating the assembly through 90° and then exerting a tensile force on the cutting wire, the end of the tip 5 of the cutting instrument can be pulled downwards as a result of which it becomes more bent, as is illustrated in FIGS. 4d and 4e. By means of the guide wire 16, the tip 5 of the catheter can be made relatively stiff, so that the vessel wall can on penetrated. It is also possible to use a puncture wire in order to penetrate the vessel wall instead of the guide wire 16. FIG. 4*f* shows the desired final state in which the occlusion 21 has been passed completely.

By pushing the loop of the cutting wire forwards and pulling it backwards, space is created for going around and/or passing the occlusion by pushing and/or separating the tissue and, if desired, the intima and media are cut. A similar effect can be achieved by moving the tip 5 itself to and fro by means of the cutting wire 6, thus creating space in order to pass the occlusion. Moreover the reciprocating movement of the tip 5 can result in a kind of scraping movement.

Figure 6:
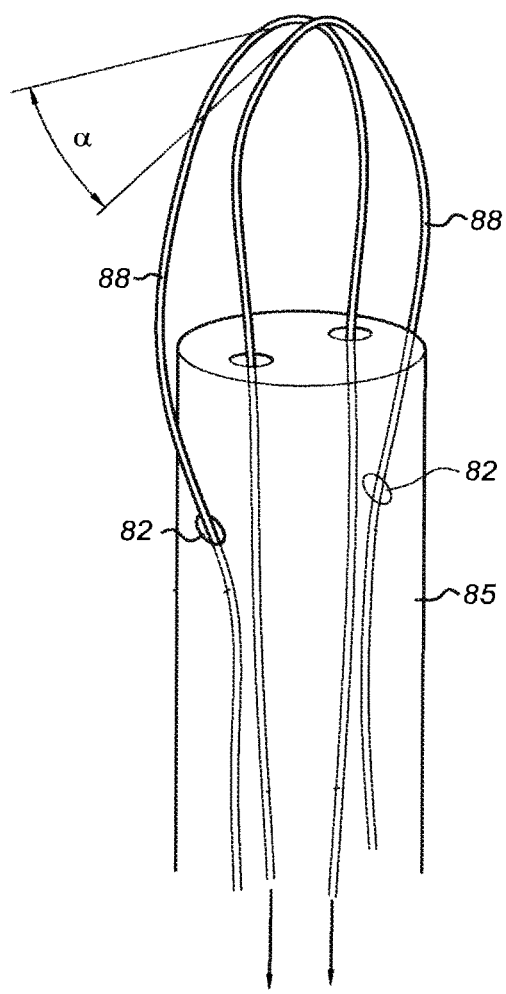
FIG. 6 shows an embodiment with two cutting wires.

FIG. 6 shows a further variant of the present invention in which two cutting wires 88 are used which extend in planes which are at an angle α to one another, with a being greater than 30°. According to one embodiment of the invention, some of the cutting wires 88 are arranged in such a manner that they extend outside the distal part. More particularly, the cutting wires extend beyond the free end of the distal part in the form of a loop, with part of the loop extending on the inside of the distal part via the free end of the distal part and the other end being situated outside thereof. The other end, which is situated outside, may be attached to the distal part at a distance from the free end thereof, for example at 82. However, it is also possible for an opening 82 to be provided at a distance from the free end of the distal part through which the cutting wire is passed to the inside.

This not only increases the number of possibilities for acting on the tissue, but eliminates the problem that the loop which is formed by the cutting wire has to be situated in a plane at right angles to the plane where the subsequent curvature illustrated in FIGS. 1-3 has to occur. This means that with this variant illustrated in FIG. 6, it is no longer necessary to rotate the sleeve through 90°, as can be seen with the transition from FIG. 4*c* to FIG. 4*d*. The flexible tip 85 can be realised such that it is substantially slack and does not have a preferred position. In other embodiments, such as for example the flexible tip 5 illustrated in FIG. 1, the flexible tip 85 is provided with a prefabricated curvature which may be situated in a plane determined by a cutting wire.

Using the above-described structure, it is possible, without requiring a further wire, to move the distal end of the flexible tip 5 at a specific location to and fro by operating the cutting wire 6 and thus to produce a certain operation. In combination with the presence of a wire, it is possible to provide steering for such a wire so that it reaches a certain position. However, it will be understood that there are numerous other possibilities which are obvious after reading the above description.

The invention claimed is:

1. A surgical cutting instrument for passing occlusions, comprising:
    a sleeve having a proximal part and a flexible tip attached to the proximal part and having a distal end, and
    a cutting wire,
    wherein said sleeve is provided with a lumen for guiding said cutting wire,
    wherein the cutting wire extends through the distal end of the flexible tip, then towards toward the proximal part on an outside of the sleeve and then contacts the flexible tip to form a loop of adjustable size,
    wherein the proximal part of the sleeve comprises a stiffer material than the flexible tip, and
    wherein the flexible tip extends from the distal end across a distance of at least 2 mm and at most 10 cm and said cutting wire is fitted in such a manner that when a force is exerted thereon, said cutting wire changes the curvature of said flexible tip.

2. The cutting instrument according to claim 1, wherein one end of said cutting wire is attached to said flexible tip.

3. The cutting instrument according to claim 2, wherein said flexible tip comprises a radiopaque material.

4. The cutting instrument according to claim 2, wherein said flexible tip comprises an external surface which is softer a core of a material of said flexible tip.

5. The cutting instrument according to claim 1, wherein one end of said cutting wire extends through an opening in said flexible tip and extends through the sleeve towards the proximal part.

6. The cutting instrument according to claim 5, wherein said flexible tip comprises a radiopaque material.

7. The cutting instrument according to claim 5, wherein said flexible tip comprises an external surface which is softer than a core of a material of said flexible tip.

8. The cutting instrument according to claim 1, wherein said flexible tip comprises a radiopaque material.

9. The cutting instrument according to claim 1, wherein said flexible tip comprises an external surface which is softer than a core of a material of said flexible tip.

10. The cutting instrument according to claim 9, wherein the flexible tip comprises a co-extrudate.

11. The cutting instrument according to claim 1, wherein said flexible tip is bent when said cutting wire is absent.

12. The cutting instrument according to claim 1, comprising two cutting wires which are provided at an angle to one another and wherein each effect the curvature of the flexible tip into continually different directions.

13. A combination comprising a surgical cutting instrument according to claim 1 and a guide wire.

14. The combination according to claim 13, wherein said sleeve comprises a further lumen for said guide wire.

15. The combination according to claim 13, wherein one end of said guide wire provides guidance in a vein and wherein an opposite end is designed as a puncturing instrument.

16. A method for passing an occlusion in a vein, comprising the steps of:
    introducing a surgical cutting instrument into said vein, the surgical cutting instrument having a sleeve having a proximal part and a flexible tip attached to the proximal part and having a distal end, the proximal part comprising a stiffer material than the flexible tip, and a cutting wire which extends from the proximal part inside the sleeve and through the distal end to an outside of the sleeve and then extends through the sleeve towards the proximal part to form a cutting loop, wherein the cutting wire is connected so that when a force is exerted thereon the cutting wire changes the curvature of the flexible tip;
    providing a passage through/past said occlusion by means of the cutting wire of the surgical cutting instrument; and
    subsequent to said introducing and providing steps, entering said vein by exerting a force on the cutting wire to bend the flexible tip so that the distal end and cutting wire extending out the distal end are directed into the vein.

17. The method according to claim 16, wherein said exerting a force on the cutting wire comprises pulling at the proximal part.

18. The method according to claim 16, comprising continuously changing the curvature of said flexible tip in order to produce a scraping movement with the distal end and the cutting wire extending out the distal end.

19. A surgical cutting instrument for passing occlusions, comprising:

a sleeve having a proximal part and a flexible tip attached to the proximal part and having a distal end, the distal end having a longitudinally directed outlet opening, and the proximal part comprising a stiffer material than the flexible tip; and a cutting wire extending from the proximal part inside the sleeve and extending through the outlet opening to an outside of the sleeve sleeve-shaped part and then extending through the sleeve towards the proximal part to form a cutting loop adjustable in size and able to cut tissue in a forward direction from the distal end, wherein the cutting wire is connected to and through the sleeve in such a way that the exerting force on the cutting wire changes a curvature of the flexible tip and directs the distal end in a direction of desired forward movement for the surgical cutting instrument.

20. The surgical cutting instrument according to claim 19, wherein the cutting wire extends through the outlet opening towards the proximal part.

* * * * *